United States Patent [19]

Amor

[11] 4,197,464
[45] Apr. 8, 1980

[54] X-RAY TABLE WITH BRACED BODY

[75] Inventor: William H. Amor, Chagrin Falls, Ohio

[73] Assignee: Picker Corporation, Cleveland, Ohio

[21] Appl. No.: 855,691

[22] Filed: Nov. 29, 1977

[51] Int. Cl.² .................... G01N 21/00; G01N 23/00
[52] U.S. Cl. ............................... 250/439 R; 250/456
[58] Field of Search ............... 250/439, 444, 445 R, 250/445 T, 446, 447, 448, 449, 450; 269/322, 323; 52/793, 785, 802, 695, 694; 108/161; 312/214

[56] References Cited

U.S. PATENT DOCUMENTS

| 2,010,971 | 8/1935 | Thomson | 52/695 |
| 3,046,638 | 7/1962 | Melzer | 52/793 |
| 3,131,301 | 4/1964 | Barrett et al. | 250/439 |

Primary Examiner—Craig E. Church
Assistant Examiner—Thomas P. O'Hare
Attorney, Agent, or Firm—Watts, Hoffmann, Fisher & Heinke Co.

[57] ABSTRACT

An X-ray table comprising a body having end, front and rear side members formed of inside and outside skin members having parts thereof spaced from one another and connected together by reinforcing members welded to the skin members and a method of making such a table. According to the method the side members are constructed as subassemblies with the inside and outside skin members of the end and front sides merely welded at their upper edges. Subsequently the vertical side members of the table body are assembled in a fixture without stress in the sheet metal parts. The outside members are then welded together at the junctures thereof. Finally the inside skin members of the end side members are welded to the reinforcing members previously welded to the end outside skin members and the front inside skin members is welded to the reinforcing members.

9 Claims, 8 Drawing Figures

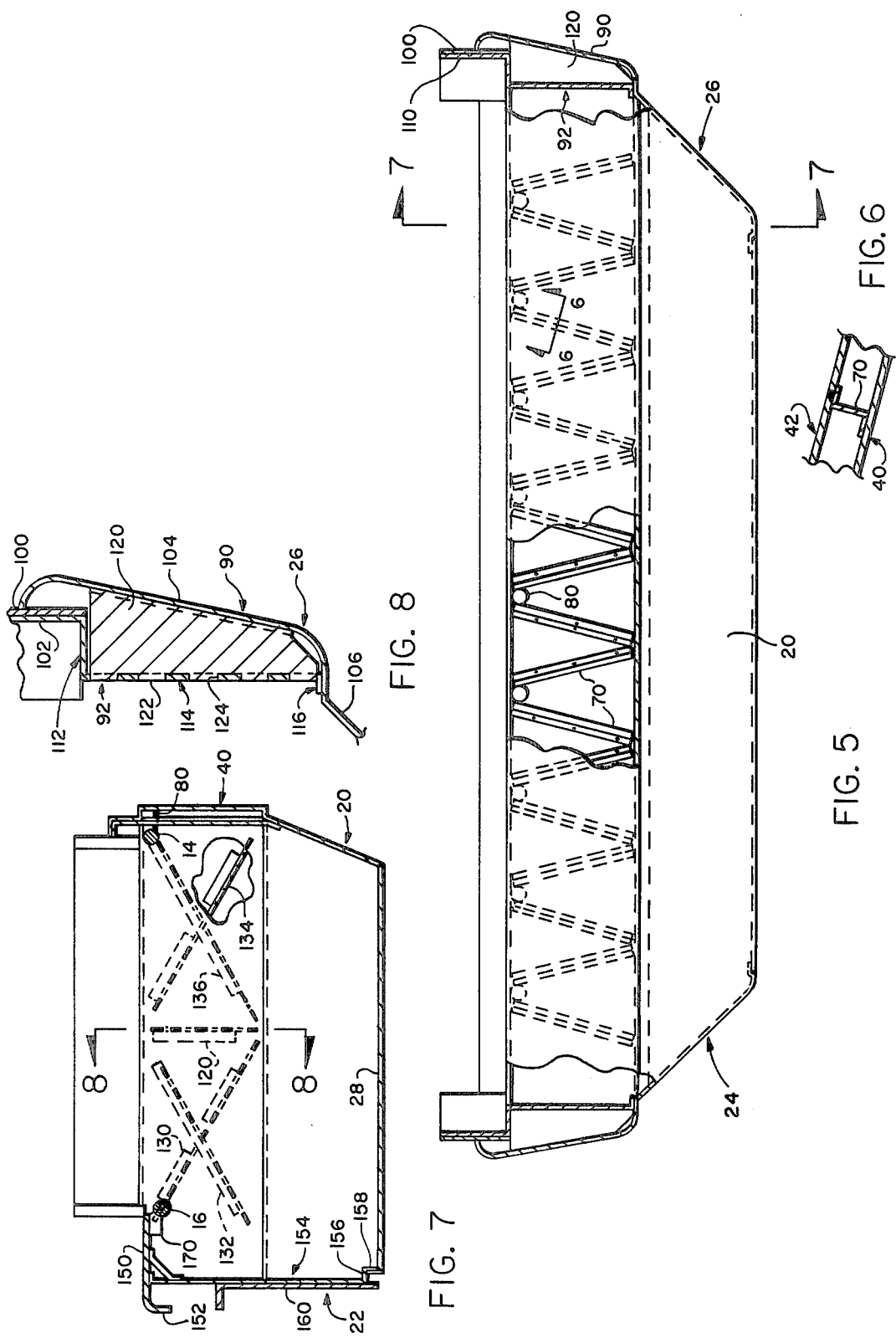

X-RAY TABLE WITH BRACED BODY

BACKGROUND OF THE INVENTION

1. Field of the Invention

The invention relates to X-ray tables and more particularly to tiltable tables preferably of the so-clled "90—90" type.

2. Description of the Prior Art

In so-called 90—90 type X-ray tables the table body is pivotally connected to a base or pedestal part so that it can be tilted 90° in either direction from its normal position in which the patient-supporting surface is horizontal. This tilting permits a patient to be examined, in any angular table body position between two vertical positions. X-ray tables of this type are well known. Such a table typically includes a movable tower assembly which supports an X-ray tube within the body. The tower also supports radiation responsive devices, such as, a spot filmer, an image tube, and cameras for viewing the image tube output. These devices are supported above the patient supporting top of the table.

The tower assembly includes a column or tower with a forwardly extending portion that extends into the body of the table and underneath the top. This tower extension is mounted on a carriage for movement horizontally in a direction transverse to the length of the table. The carriage is in turn supported on suitable ways in the body of the table for movement lengthwise of the table proper. The tower projects from the rear of the table body and supports a column or tower upon which a further carriage is supported for movement towards and from the table proper. The further carriage carries the radiation detection device which is also movable throughout substantially the entire length of the table.

The movement of a tower assembly should be smooth and relatively effortless. It also should be linear to maintain accurate and consistent spatial relationship among a patient, the table's X-ray tube and the supported imaging devices. If the movement of the tower assembly and the table top is to be consistent and linear the table must be rigid and accurately manufactured.

Conventionally, tables have been constructed in which an upper frame and connected or integrally formed track elements supported the tower assembly. Such a frame was rigidified by a relatively stiff table top. Body sides and ends of such a table, if provided at all, were little more than a sheet metal shroud which improved the table appearance and afforded some X-ray shielding.

With the advent of movable table tops which are powered, and which have become quite popular, the described conventional table construction became obsolete. Table strength now must be provided by the table body which must be strong enough not only to make up for the stiffening formerly supplied by a table top but also to support the top and the motor and drive assembly which carry and move it.

The problem of table body construction is made even more difficult because the weight of imaging devices which must be supported by the tower assembly, and counterweighted in the table body to accomodate the heavier imaging weights, has steadily increased over the years. Since the interior of the table body must be sufficiently open to permit unrestricted tower assembly and counterweight movement the needed strength must be provided in the body walls.

Prior to the present invention various table constructions have been employed, but none are entirely satisfactory. For example, weldments have been used but these have tended to warp due to stress developed during welding operations and to buckle when placed under load.

SUMMARY OF THE INVENTION

The present invention provides a novel and improved X-ray table, preferably of the 90—90 type pivotally supported on a base or pedestal, cantilevered thereon, if desired, for movement from one vertical position to the opposite vertical position and which table is relatively light in weight and will not flex in use.

The invention resides in certain constructions and combinations and arrangements of parts and further objects and advantages of the invention will be hereinafter referred to and others will be apparent from the following description of the preferred embodiment of the invention depicted in the accompanying drawings.

BRIEF DESCRIPTION OF THE DRAWINGS

FIG. 5 is a front elevational view of the body of the table, with parts broken away and parts in elevation;

FIG. 6 is a fragmentary sectional view approximately on the line 6—6 of FIG. 5;

FIG. 7 is a sectional view of the body of the table approximately on the line 7—7 of FIG. 5; and FIG. 8 is a sectional view approximately on the line 8—8 of FIG. 7.

DESCRIPTION OF THE PREFERRED EMBODIMENT

Figure 1:
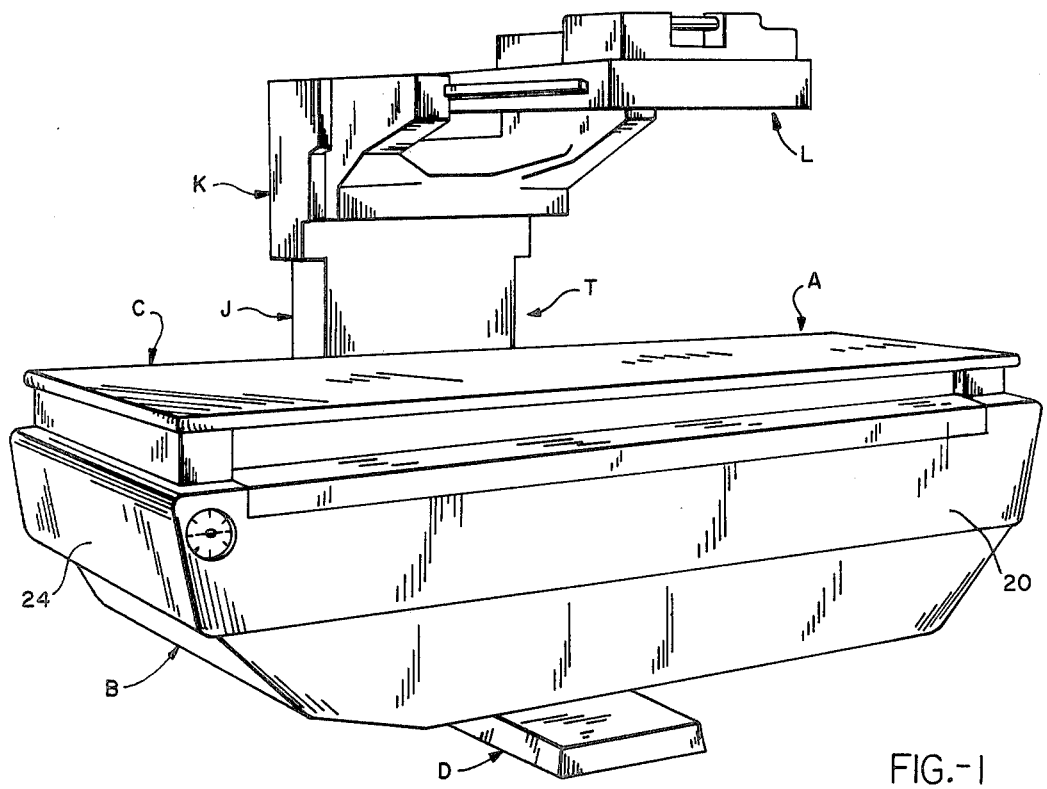
FIG. 1 is a perspective view of a 90—90 X-ray table assembly embodying the present invention.
Figure 3:
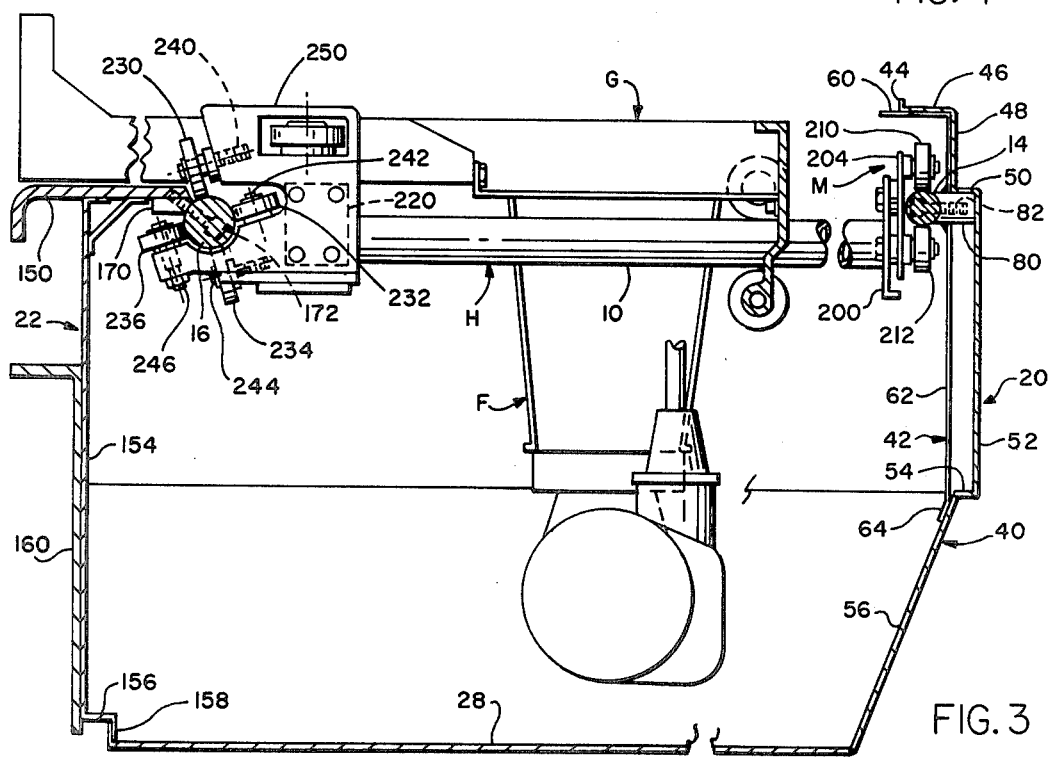
FIG. 3 is a fragmentary sectional view, with parts in elevation, approximately on the line 3—3 of FIG. 2 and looking towards the right, that is, in the direction of the foot of the table.
Figure 2:
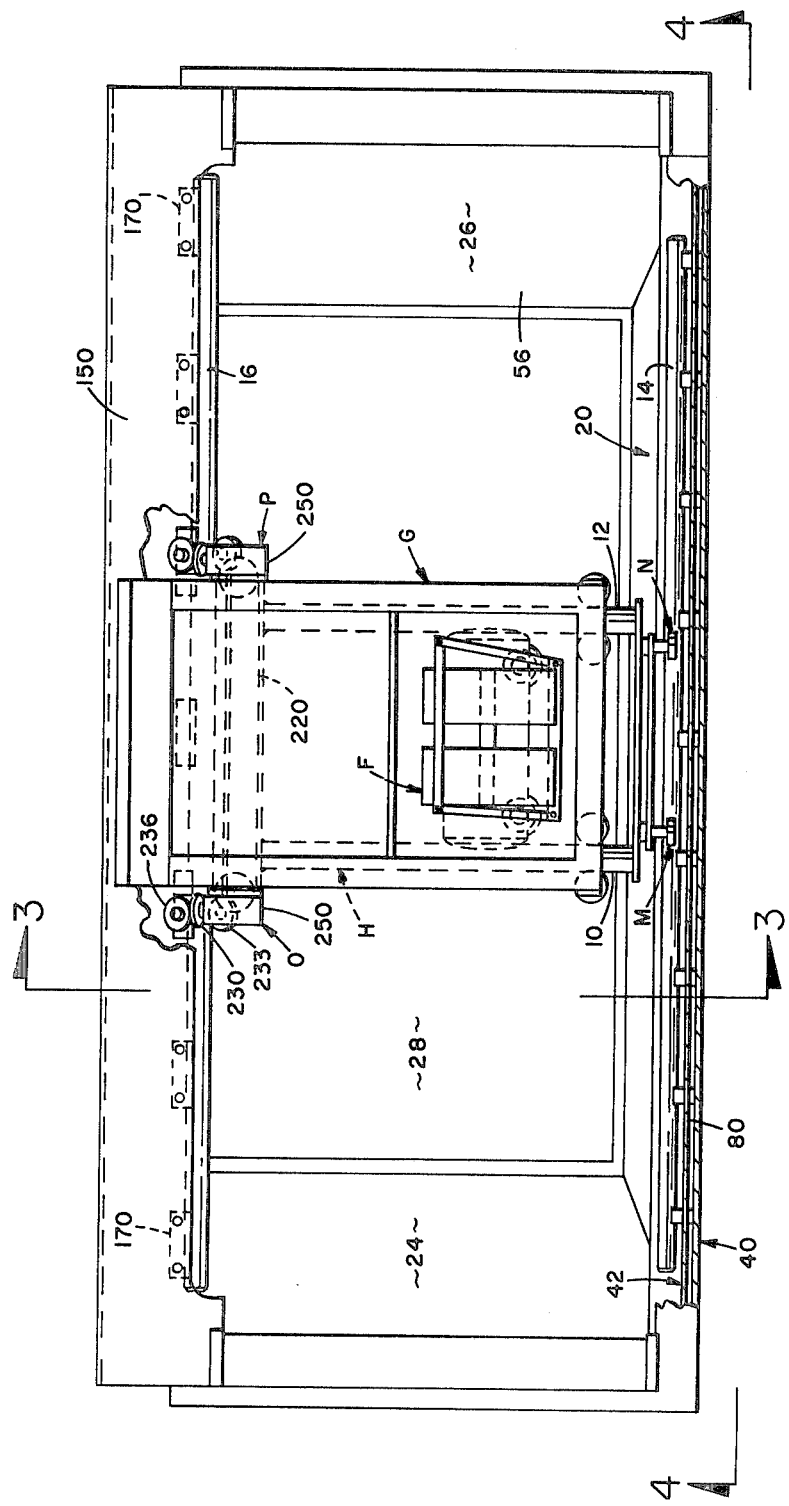
FIG. 2 is a fragmentary plan view of the body of the table with the patient supporting top removed and parts broken away.
Figure 4:
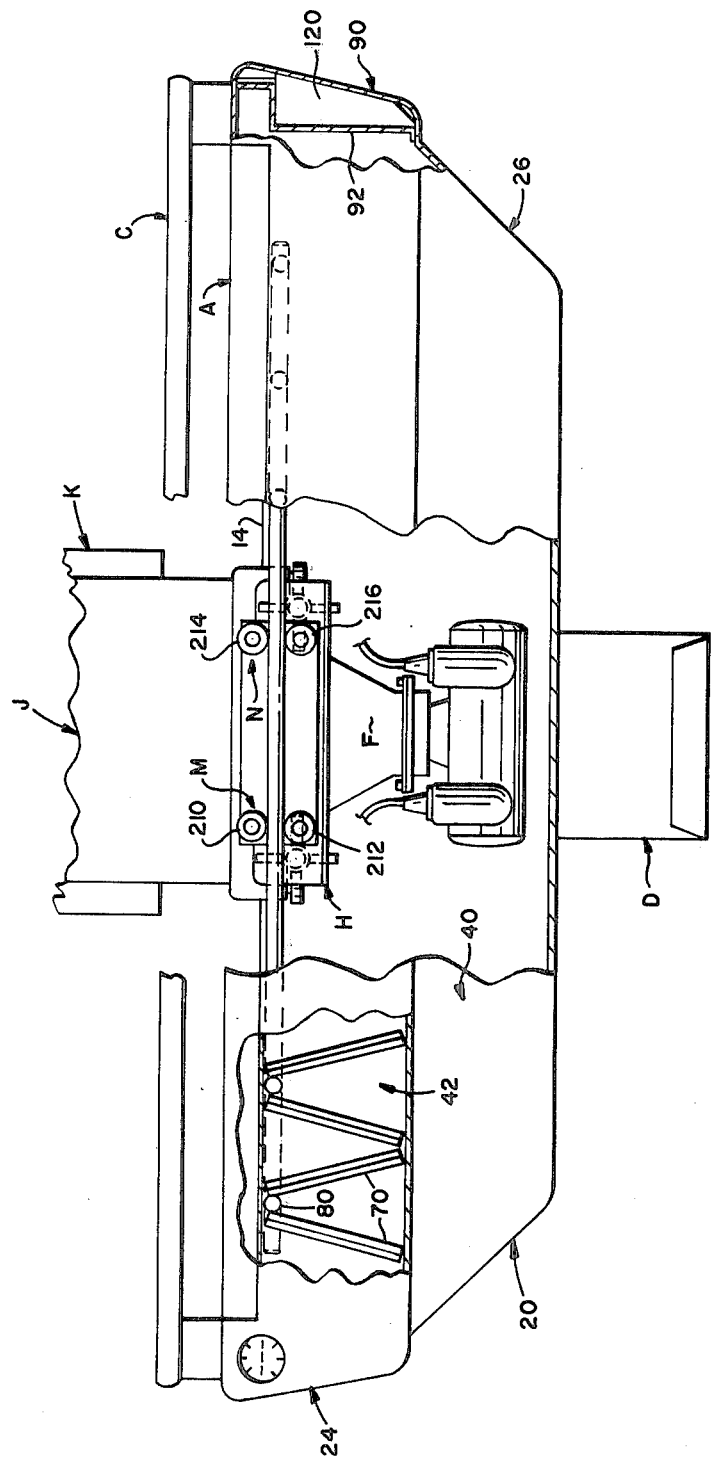
FIG. 4 is a sectional view, with parts broken away and parts in elevation, approximately on the line 4—4 of FIG. 2.

Referring to the drawings FIG. 1 is a perspective view of an X-ray table of the 90—90 type embodying the present invention which is concerned primarily with the construction of the "tub" or body part of the table proper. The X-ray table is designated generally by the reference character T and comprises a table proper designated generally by the reference character A which includes a body B having a patient supporting top C. The table A is pivotally supported on a base part or pedestal D only a part of which is shown. The table A is cantilevered from the rear part of the pedestal D.

In the depicted table A the X-ray tube is in a holder F within the body of the table on a column or tower carriage G transversely movable of the table body on ways or supports 10, 12 forming part of a carrier H movable longitudinally of the table body on ways or supports 14, 16 in the table body. The tower carriage G extends rearwardly from the table body and carries, on its outward projection, a tower or column J which in turn supports a carriage K for vertical movement along the tower. The carriage K in turn supports a radiation detector carrier L movable transversely of the table proper A.

The particular construction of the X-ray table T, other than the table body B, forms no part of the present invention and may be of any commercial or known construction. The particular manner of supporting the tower carriage G in the table body B is the subject of a patent application of Edward T. Schneider entitled "X-ray Table" and filed on even date herewith. As for the present invention the tower carriage G may be supported in any suitable manner.

The four vertical front, rear, head end and foot end sides 20, 22, 24, 26 of the table B are constructed as sub-assemblies and then placed in a suitable fixture or jig and welded together. The bottom 28 is subsequently welded to the lower parts of the vertical sides of the table. After installation of the tower carriage ways 14, 16 and the other parts of the table located within the body B the table top C is installed.

The front side 20 of the table B comprises an outside sheet metal member 40 and an inside sheet metal member 42 commonly referred to as the front side outside and inside skins, respectively. The outside member 40 forms the front outside of the table. The front outside skin has a short vertical flange 44 along its upper edge extending upwardly at right angle from a rather narrow horizontal panel 46 formed integral with an upper edge of rather narrow vertical panel 48. At the lower edge of panel 48 the member 42 bends horizontally to form a narrow horizontal panel 50 and then downwardly at right angles to the panel 50 to form a rather wide vertical panel 52 then inwardly at right angles to the panel 52 to form a second rather narrow horizontal panel 54 then downwardly and inwardly at a slight angle to form a lower inwardly inclined or sloping panel 56. The front inside skin 42 has a horizontal panel 60 abutting the underside of panel 46 and extending slightly inwardly of vertical panel 44. From panel 60 the member 42 bends downwardly at right angles to panel 60 to form a vertical panel 62. Panel 62 extends downwardly along the inside of the front outside member 40 to slightly beyond horizontal panel 54 and terminates in a relatively narrow panel 64 inclined inwardly at an angle the same panel 56.

Prior to assembly of the members 40, 42 with one another, rod-like reinforcing or stiffening members 70 Z-shaped in cross-section are welded to the rear side of panel 52 of member 40. The members 70, of which there are eighteen in the depicted table, are slightly inclined to the vertical and arranged in a zig zag fashion with adjacent members inclined in opposite directions. Members 70 extend from panel 50 to panel 54 of member 40 with a space between the upper ends of each pair of members. The members 40, 42 are assembled with one another and welded at the top. There-after cylindrical members 80 are inserted in suitable through apertures in members 42 between upper end of members 70 which ends are closest together. The members 80 of which there are nine in the depicted table form supports as will be hereinafter more specifically described for the tower carriage front way 14. The openings in member 42 through which the members 80 project are slightly larger than the members 80 so that members 80 can be aligned with one another as they are welded to member 42. Later the inner ends of members 80 have horizontally aligned duplicate V-grooves machined therein for the reception of the way 14 which is an accurately formed cylindrical bar. The way 14 is fixed to the members 80 by countersunk head screws 82 threaded in tapped apertures in members 80.

The head and foot ends 24, 26 of the table body B are generally similar in construction and merely the foot end 26 is described in detail. Like the front side of the table B the foot end comprises outside and inside sheet metal members 90, 92 hereinafter sometimes referred to as the head end outside and inside skin, respectively. The upper edge of the outside skin member 90 is welded to a vertical member 100 having a narrow vertical panel 102 at its upper end. From the member 100 the member 90 curves downwardly and inwardly to a planer panel 104 which is inwardly inclined, at the lower end of panel 104 member 90 curves inwardly and then downwardly and inwardly to form a planar panel 106 which terminates at the bottom of the table B. The inner skin 92 has an upper vertical panel 110 which abuts member 102. At the lower end of panel 110 member 92 bends inwardly at right angle and forms horizontal panel 112 and then downwardly at right angles to form vertical panel 114 and terminates in a horizontal panel 116 welded to the lower end of panel 104 of member 90.

Before members 90 and 92 are assembled for welding one to the other, reinforcing members are welded to the inside of panel 104 of the outside skin member 26. One of these reinforcing members is a vertical plate 120 which extends from the panel 112 to the lower end of panel 114 of the inside skin member 92, and which is located intermediate the front and rear sides of the table. The edge of the plate 120 adjacent to the panel 104 is welded thereto and the opposite edge has a plurality of tabs 122 adapted to extend through apertures 124 in the inside skin member 92. Pairs of diagonal cross braces 130, 132 and 134, 136 are also welded to the inside of the panel 104 of the outside skin member 90. Like the inner edge of the reinforcing member 120, the inner edges, that is, the edges of the cross braces not adjacent to the outside skin member 90 are provided with tabs similar to the tabs 122 of the member 120, which tabs are inserted in suitable apertures or slots in the inside skin member 92. After the reinforcing members 120, 130, 132, 134, 136 are welded to the inside of the outside skin member 104, the skin members 90, 92 are assembled together with the tabs on the aforementioned reinforcing members extending through the previously-mentioned slots in the inside skin member 52 and the upper edge of the outside skin member 90 is welded to member 100 and the upper edge of the inside skin member 92 is also welded to the member 100 thus maintaining the inside and outside skin members together.

The rear side 22 of the body 20 of the table 2 comprises a longitudinally extending horizontal member 150 having a flange 152 along its rear edge which extends downwardly at right angles to the horizontal part of the member 150. A rear vertical panel member 154 having a narrow flange at its upper edge is welded to the underside of the member 150 and the lower end thereof terminates in a narrow, horizontal panel 156, the inner end of which terminates in a narrow vertical panel 158. A heavy reinforcing vertical member 160 extending longitudinally of the table is welded to the outside of the member 154.

With the vertical rear sides of the body 20 of the table B assembled as mentioned above, they are assembled in a jig or fixture with the outer corner thereof aligned in such a manner that no stress is incurred in the sheet metal parts thereof. During this assembly the inner skins of the front member 20 and the end members 24, 26 are free to float relative to the outer skins thereof because the tabs of the reinforcing members 120, 130, 132, 134 are smaller than the apertures in the inner skin members through which they project. With the parts thus assembled the reinforcing members in the ends of the table are welded to the inner skins at opposite ends and the adjoining corners of the vertical sides are welded together and the member 42 is plug welded to the stiffening members 70. When the tub or body of the table is removed from the jigger fixture, the tub or body will not warp because no stress had been set up therein. The bottom member 28 is subsequently welded to the lower edges of the vertical side members.

As previously mentioned the tower carriage front way 14 is supported or carried by members 80 at the front of the table body 20. The rear tower carriage way 16 which is also an accurately formed cylindrical bar is connected to the table B along the rear upper inside edge thereof by a plurality of bracket members 170 of which there are seven (7) in the depicted table. The members 170 are spaced along the rear side of the table and are bolted to the underside of the member 150. The members have V grooves machined in their inner sides which are inclined downwardly and outwardly for the reception of the way 16 which is bolted to the bracket by machine screws 172.

The tower carriage H is supported on the ways 14, 16 by roller assemblies M, N, O, P located at the front head and foot corners of the tower carriage and at the head and foot sides of the carriage adjacent to the rear of the table B, respectively. The front ends of the tower carrier ways 10, 12 are welded to a vertical plate 200 having a forwardly extending horizontal flange along its lower edge. A longitudinally extending vertical plate 204 is connected to the plate 200 and spaced therefrom by suitable spacers. A top roller 210 rotatably supported on a stub shaft welded to the plate 204 engages and rides upon the top of way 14. A similar roller 212 rotatably supported by a stud shaft connected to the plate 204 by an adjustable eccentric bearing engages the lower side of the way 14. Upper and lower rollers 214, 216 similar to rollers 210, 212 and connected to plate 204 at the foot end of carriage H in like manners engage and travel along the top and bottom sides respectively of the way 14.

The rear ends of ways 10, 12 extend through a rectangular tubular member 220 extending lengthwise of the table B adjacent to the rear side of the table. The roller assemblies O, P for supporting the carriage H on the rear way 16 are alike except for differences incident to their being connected to opposite ends of the member 220 and merely assembly O adjacent to the head end of the table B will be described.

Roller assembly O comprises four rollers 230, 232, 234, 236 spaced ninety degrees (90°) apart about the way 16. The rollers are carried on stub shafts 240, 242, 244, 246, respectively, connected to a bracket 250 connected to the head end of member 220. Rollers 230, 234 line in a plane which makes an angle of about thirty degrees (30°) with a vertical plane through the center of way 16 from which it will be evident rollers 230, 232 engage the upper surface of the way 16. Rollers 234, 236 engage the lower surface of the way 16. The lower rollers 234, 236 are eccentrically connected to the bracket 250 so that they can be adjusted relative to the way 16.

From the foregoing description of the preferred embodiment of the invention it will be apparent that an X-ray table body has been provided which is relatively inexpensive to construct, is light in weight, is free from stresses in the sheet metal parts therein, and which will not warp during use.

While the preferred embodiment of the invention has been described in considerable detail, it will be apparent that the invention can be otherwise incorporated and it is the intention to hereby cover all adaptations, modifications and uses thereof which come within the scope of the appended claims.

I claim:

1. In a tiltable X-ray table of the type wherein a body is supported on a pedestal for tiltable movement and a powered top is carried by the body, a table body construction comprising:
   (a) a front subassembly including spaced inner and outer panels;
   (b) a spaced pair of end subassemblies each including spaced inner and outer panels;
   (c) the subassemblies being secured together with the front subassembly connected to both end assemblies;
   (d) rear frame structure connected to the end subassemblies and spaced from the front subassembly to provide a tubular body;
   (e) each of the end subassemblies including cross bracing between and fixed to each of its panels;
   (f) the front subassembly including a bracing comprising a plurality of members arranged in zigzag fashion with successive pairs, each pair forming a "V" shaped configuration with the members of each pair being substantially in abutment at their lower ends and each pair being spaced at the top from a successive pair; and,
   (g) a plurality of carriage supports each positioned between the upper ends of successive pairs of members and secured thereto as by welds.

2. In a tiltable X-ray table of the type wherein a body is supported on a pedestal for tiltable movement and a powered top is carried by the body, a table body construction comprising:
   (a) a front subassembly including spaced inner and outer panels;
   (b) a spaced pair of end subassemblies each including spaced inner and outer panels;
   (c) the subassembly being secured together with the front subassembly connected to both end assemblies;
   (d) rear frame structure connected to the end subassemblies and spaced from the front subassembly to provide a tubular body;
   (e) each of the end subassemblies including cross bracing between and fixed to each of its panels; and,
   (f) the front subassembly including bracing comprising a plurality of members arranged in zigzag fashion with successive pairs, each pair forming a "V" shaped configuration with the members of each pair being substantially in abutment at the lower ends and each pair being spaced at the top from a successive pair.

3. The table body of claim 2 wherein each end subassembly further includes a reinforcing member, the reinforcing member being a plate transverse to and fixed to the spaced inner and outer panels.

4. The table body of claim 3 wherein the plate reinforcing member of each end subassembly has a portion that extends through the inner panel of that end subassembly.

5. The table body of claim 3 wherein each cross bracing extends substantially parallel to the spaced inner and outer panels.

6. In a tiltable X-ray table of the type wherein a body is supported on a pedestal for tiltable movement and a powered top is carried by the body, a table body construction comprising:
   (a) a front subassembly including spaced inner and outer panels;
   (b) a spaced pair of end subassemblies;
   (c) the subassemblies being secured together with the front subassembly connected to both end subassemblies;
   (d) rear frame structure connected to the end subassemblies and spaced from the front subassembly to provide a tubular body; and,
   (e) the front assembly including a bracing comprising a plurality of members arranged in zigzag fashion with successive pairs, each pair forming a "V" shaped configuration with the members of each pair being substantially in abutment at their lower ends and each pair being spaced at the top from a successive pair.

7. In a tiltable X-ray table of the type wherein a body is supported on a pedestal for tiltable movement and a powered top is carried by the body, a table body construction comprising:
   (a) a front subassembly including spaced inner and outer panels;
   (b) a spaced pair of end subassemblies each including spaced inner and outer panels;
   (c) the subassemblies being secured together with the front subassembly connected to both end assemblies;
   (d) rear frame structure connected to the end subassemblies and spaced from the front subassembly to provide a tubular body;
   (e) at least one of the subassemblies including bracing between and fixed to each of its panels; and,
   (f) the bracing of said at least one subassembly including a plurality of elongate members, at least some of the members being secured to the inner and outer panels of said one subassembly at locations spaced longitudinally of the secured members.

8. The panels of claim 7 wherein each such panel has such elongate members secured at spaced locations.

9. In a tiltable X-ray table of the type wherein a body is supported on a pedestal for tiltable movement, a table body construction comprising:
   (a) a front subassembly including spaced inner and outer panels;
   (b) a spaced pair of end subassemblies each including spaced inner and outer panels;
   (c) the subassemblies being secured together with the front subassembly connected to both end assemblies;
   (d) rear frame structure connected to the end subassemblies and spaced from the front subassembly to provide a tubular body;
   (e) the front subassembly including a bracing comprising a plurality of members arranged in zigzag fashion with successive pairs, each pair forming a "V" shaped configuration with the members of each pair being substantially in abutment at their lower ends and each pair being spaced at the top from a successive pair;
   (f) each of the end subassemblies including cross bracing between and fixed to each of its panels, each cross bracing extending substantially parallel to the spaced inner and outer panels of that end subassembly; and,
   (g) each of the end subassemblies further including a reinforcing member, the reinforcing member being a plate transverse to and fixed to the spaced inner and outer panels of that end assembly, wherein the plate reinforcing member of said each end subassembly includes a portion that extends through the inner panel of that end subassembly.

* * * * *